(12) United States Patent
Lekutai et al.

(10) Patent No.: US 9,047,648 B1
(45) Date of Patent: Jun. 2, 2015

(54) MEASUREMENT, COLLECTION, REPORTING AND PROCESSING OF HEALTH CONDITION DATA

(75) Inventors: Gaviphat Lekutai, Kirkland, WA (US); Alan Denis MacDonald, Bellevue, WA (US)

(73) Assignee: AT&T MOBILITY II LLC, Atlanta, GA (US)

( * ) Notice: Subject to any disclaimer, the term of this patent is extended or adjusted under 35 U.S.C. 154(b) by 1706 days.

(21) Appl. No.: 11/393,328

(22) Filed: Mar. 30, 2006

(51) Int. Cl.
*G06Q 50/00* (2012.01)
*G06Q 50/22* (2012.01)
*G06Q 50/24* (2012.01)
*G06Q 10/02* (2012.01)

(52) U.S. Cl.
CPC ............... *G06Q 50/22* (2013.01); *G06Q 50/24* (2013.01); *G06Q 10/02* (2013.01)

(58) Field of Classification Search
USPC ........... 455/403; 600/300; 705/2, 3; 235/380; 604/66
See application file for complete search history.

(56) References Cited

U.S. PATENT DOCUMENTS

| | | | | |
|---|---|---|---|---|
| 5,983,193 | A * | 11/1999 | Heinonen et al. | 705/2 |
| 6,302,844 | B1 * | 10/2001 | Walker et al. | 600/300 |
| 7,421,285 | B1 * | 9/2008 | Rao et al. | 455/557 |
| 2001/0031913 | A1 * | 10/2001 | Ito et al. | 600/300 |
| 2001/0051787 | A1 * | 12/2001 | Haller et al. | 604/66 |
| 2002/0091547 | A1 * | 7/2002 | Ohe et al. | 705/2 |
| 2003/0233250 | A1 * | 12/2003 | Joffe et al. | 705/2 |
| 2004/0122702 | A1 * | 6/2004 | Sabol et al. | 705/2 |
| 2004/0151379 | A1 * | 8/2004 | Kim et al. | 382/209 |
| 2004/0199409 | A1 * | 10/2004 | Brown | 705/3 |
| 2004/0229595 | A1 * | 11/2004 | Laursen et al. | 455/403 |
| 2004/0260577 | A1 * | 12/2004 | Dahlin et al. | 705/2 |
| 2005/0203349 | A1 * | 9/2005 | Nanikashvili | 600/300 |
| 2006/0106646 | A1 * | 5/2006 | Squilla et al. | 705/3 |

* cited by examiner

*Primary Examiner* — Valerie Lubin
(74) *Attorney, Agent, or Firm* — Amin, Turocy & Watson, LLP

(57) ABSTRACT

Systems and methods for measuring, collecting, managing, reporting and distributing data pertaining to medical device measurements, such as personal health condition data, are provided. In various embodiments, medical device(s) are paired (integrated, tethered, or wirelessly coupled) with a user's portable computing device, such as a cell phone, so that the portable device receives locally made health data measurement(s) recorded by the medical device(s). After any pre-processing by the portable device, standard interfaces enable the health data measurement(s) to be transmitted, e.g., periodically, from the portable device to a health station server on a wireless communications network. The health station server may then analyze the health data measurement (s), e.g., versus historical and demographic data, so that the results of the analysis can be distributed to end users and service providers alike who make use of the communications network in a variety of ways.

26 Claims, 11 Drawing Sheets

MEASUREMENT, COLLECTION, REPORTING AND PROCESSING OF HEALTH CONDITION DATA

FIELD OF THE INVENTION

The present invention is directed to communication services for medical devices. More particularly, the present invention is directed to systems and methods of measuring, collecting, reporting and processing health condition data via wireless portable devices.

BACKGROUND OF THE INVENTION

Historically, people interested in monitoring aspects of their health have had few options in terms of finding an integrated system that is easy to use, inexpensive, customizable, private and portable. A primary way that people currently monitor their health is by making a trip to a doctor, or hospital. Hospitals and other medical institutions are loaded with equipment that measures health condition data, and such data can be instantly processed in some cases, or otherwise interpreted on-site, to help determine health risks for people that use the equipment on-site. However, this option has always been relatively expensive because not only is the measuring equipment expensive, but other hospital overhead is expensive, not to mention the cost of a doctor's or nurse's time, and loss of one's own time, which all factor into the overall expense of receiving health related data on-site at medical institutions. Accordingly, going to a doctor to receive health related condition information can be an extremely costly measure, especially if all one wants to do is make a rudimentary determination that a certain known health condition is within a normal range, or in check, for instance.

In other places in the market, standalone exercise equipment is sometimes outfitted with health meter(s) whereby, for example, a user making physical contact with a hand grip of the equipment can observe near instantaneous feedback on display about his or her heart rate in relation to optimal exercise conditions for that user and equipment based on conditions such as age and weight of the user. Such standalone exercise equipment, however, is not inexpensive and clearly not portable. Moreover, the software it comes with is not customizable, and the display of such equipment is not particularly private in that any on-looker can take a look at a neighboring display. Finally, such data is not stored so that an individual's data can be examined over long periods of time. Still further, there is no way for these devices to automatically notify health officials in the event of a health emergency.

Other standalone health measurement devices might be portable, but nonetheless suffer other drawbacks. For example, some medical devices can be attached to a user's wrist, or otherwise to a user's body, so that a user can record health condition data while jogging. Some wrist watches include the ability to measure heart rate while a user wears the watch, for instance. However, such portable standalone medical devices suffer some similar drawbacks. For instance, the software is not customizable or updatable after the point of sale of the device. The data is not stored for historical viewing of the data, and is not reported to anywhere in the event of a health emergency. Similarly, home kits exist for measuring sugar levels by diabetics, and the like, however, none of these medical devices report the data in any meaningful sense to health professionals who may be able to help in the event of an unstable health condition.

Bluetooth technology has also been applied to some medical devices with the ability to communicate measured data via Bluetooth to other Bluetooth enabled devices. However, such devices thus far have been used in only limited scenarios.

In addition, today, if a user is aware of a health emergency, to receive immediate care, a user can call 9-1-1, though such a call may require consciousness, mobility and clear communication which may not be possible in the event of birth, or cardiac arrest. In addition, some products provide a proprietary closed loop emergency care system, whereby a person facing a serious health risk is given an "emergency button" available to the person. For instance, the emergency button can be kept on a person, or hung on a necklace, or the like, so that if the person experiences a health emergency, a simple press of the button notifies a centralized system. However, the emergency button system does not apprise the health professionals of the cause for emergency, or what health conditions directly preceded the emergency. In addition, such systems do not generalize to a variety of medical devices via standard interfaces.

Alternate techniques for directly measuring health condition data in a more immediate and relevant/accurate fashion are thus desirable. It would be further desirable to provide versatility, connectivity, and accuracy of health condition data via wireless mobile devices or similar portable devices. It would be further desirable to provide a service based on such reporting of health condition data to provide accurate real-time information and services to portable device users, based on their profile. It would be further advantageous to optionally provide the above-described benefits without requiring packet switch services (e.g., TCP/IP packet services) in order to enable the automatic collection and delivery of health data and services via a wireless data communications network. It would be still further desirable to improve upon control/voice interfaces and infrastructures for portable wireless devices to enable the delivery of periodic measurements from a client node within a network to a health station server, and to enable services to automatically initiate in response to results of the health condition data collected for a user or in response to pre-defined patterns found in the health condition data.

SUMMARY OF THE INVENTION

For improved reliability and relevancy of reporting of health condition data, fast access to health data, and consistent collection of health data, systems and methods for measuring, collecting, managing, reporting and distributing data pertaining to medical device measurements, such as personal health condition data, are provided. In various embodiments, medical device(s) are paired (integrated, tethered, or wirelessly coupled) with a user's portable computing device, such as a cell phone, so that the portable device receives locally made health data measurement(s) recorded by the medical device(s). After any pre-processing by the portable device, standard interfaces enable the health data measurement(s) to be transmitted, e.g., periodically, from the portable device to a health station server on a wireless communications network. The health station server may then analyze the health data measurement(s), and/or versus historical and demographic data so that the results of the analysis can be distributed to end users and service providers alike who make use of the communications network in a variety of ways. In one embodiment, the collection, distribution and reporting of the health condition data to and from the health station server does not rely on the need for TCP/IP network connectivity, since voice/data, control and broadcast channels of an applicable mobile communications network may be utilized.

Other features of the invention are described in more detail below.

BRIEF DESCRIPTION OF THE DRAWINGS

The health data services and reporting systems in accordance with the invention are further described with reference to the accompanying drawings in which.

DETAILED DESCRIPTION OF ILLUSTRATIVE EMBODIMENTS

Overview

Figure 1A:
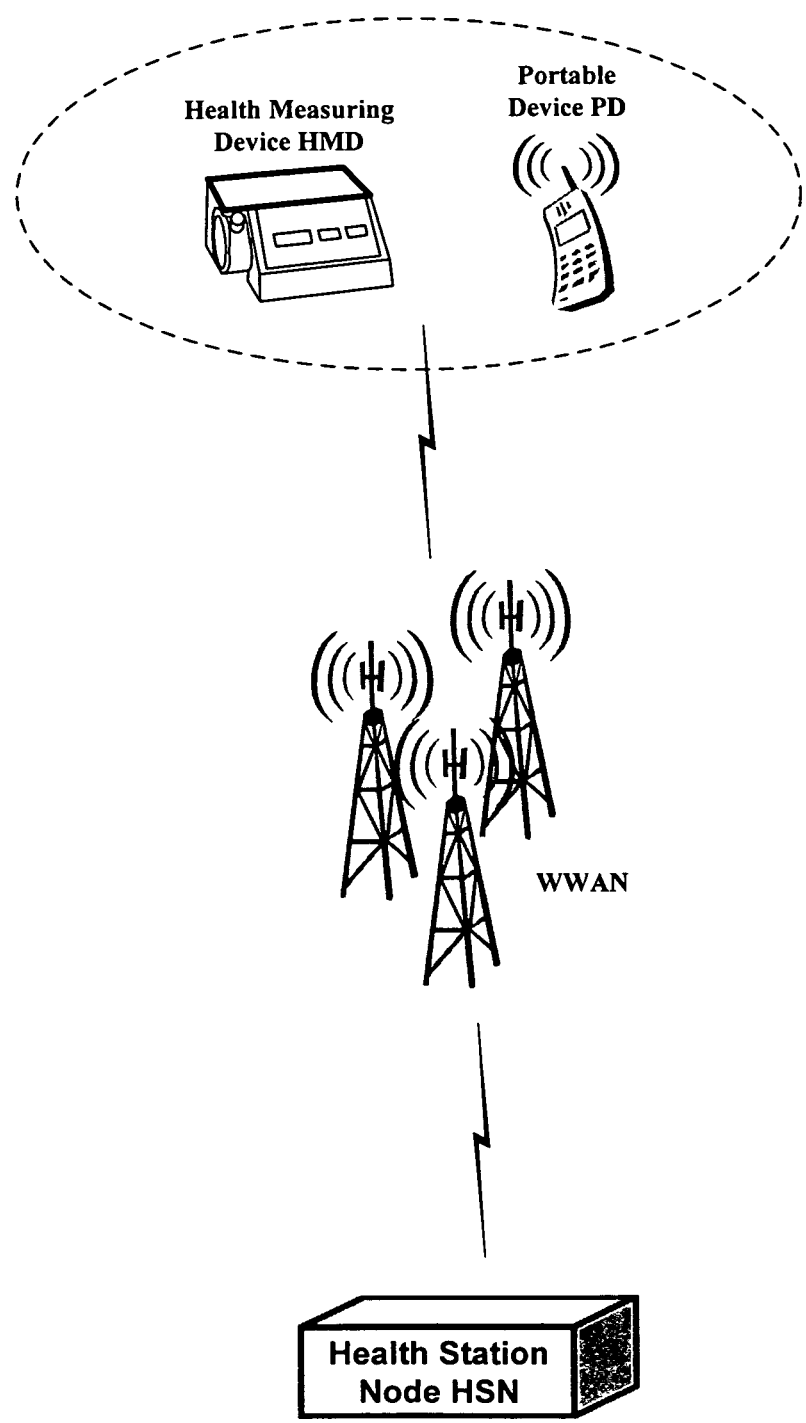
FIG. 1A illustrates an overview of the framework for the health data services of the present invention.

As described in the background, while health monitoring devices exist, there are a number of shortcomings of such systems due to lack of flexibility, inaccessibility of the data and non-integration with any other systems (closed-loop systems) according to such existing techniques.

In consideration of these and other shortcomings, the invention provides an alternative technique that measures health data for a user, receives the health data via a portable device of the user, and seamlessly transmits the health data from the portable device to a networked computing environment, where powerful scenarios emerge, e.g., automatically alerting health professionals of emergencies, and allowing a user unrestricted access and display of historical data applying to the user. In various embodiments described below in more detail, the invention provides systems and methods for measuring health condition data by pairing health data measuring devices directly or indirectly with networked portable devices, such as mobile handsets, and by providing storage and processing of the health data in at least one node of the network, i.e., a health data service.

The invention thus provides versatility, connectivity, relevancy and accuracy of health station reporting via wireless mobile or similar devices. Via various non-limiting embodiments described below, the invention enables health reporting services such that users of portable devices, such as voice users of a cellular phone, do not have to switch to packet switch services (if the users even have such packet switch services) to utilize the health data reporting services of the invention. In one non-limiting embodiment, the invention provides an architecture that improves upon existing control/voice interfaces and infrastructures to send specific periodic measurements to a health reporting server node, which aggregates and manages health reporting data on behalf of the subscribers of the network. Since the invention (A) improves upon existing interfaces, (B) allows a variety of health measurement devices to communicate with a portable device, and (C) leverages existing towers and networks for health data aggregation, the invention enables health reporting services for a variety of health data measurement devices via a wireless network for all end users who utilize the wireless network.

Health station storage devices can be placed at various places around the network, to store and/or process the health station data in some fashion. In a wireless communications network, such health station device(s) can be integrated into a tower shelter which houses equipment for the base station subsystem, the radio network controller (RNC), and/or NodeB, and can connect to control interfaces. A new additional network node, i.e., the "health station" or "health data server," is thus introduced by the invention, which collects health data measurements periodically on behalf of users of the network, and processes the data for further applications. The health station server node may include one or more computers, however distributed across the network.

Exemplary Non-Limiting Network and Operating Environments

The following description sets forth some exemplary networks and non-limiting operating environments for the health condition data collection and reporting services of the present invention. The below-described operating environments should be considered non-exhaustive, however, and thus the below-described network architectures merely show how the services of the present invention may be incorporated into existing network structures and architectures. One can appreciate, however, that the invention may be incorporated into now existing or future alternative architectures for communication networks as well.

The global system for mobile communication ("GSM") is one of the most widely utilized wireless access systems in today's fast growing communication systems. GSM provides circuit-switched data services to subscribers, such as mobile telephone or computer users. General Packet Radio Service ("GPRS"), which is an extension to GSM technology, introduces packet switching to GSM networks. GPRS uses a packet-based wireless communication technology to transfer high and low speed data and signaling in an efficient manner. GPRS optimizes the use of network and radio resources, thus enabling the cost effective and efficient use of GSM network resources for packet mode applications.

As one of ordinary skill in the art can appreciate, the exemplary GSM/GPRS environment and services described herein can also be extended to 3G.services, such as Universal Mobile Telephone. System ("UMTS"), Frequency Division Duplexing ("FDD") and Time Division Duplexing ("TDD"), High Speed Packet Data Access ("HSPDA"), cdma2000 1x Evolution Data Optimized ("EVDO"), Code Division Multiple Access-2000 ("cdma2000 3x"), Time Division Synchronous Code Division Multiple Access ("TD-SCDMA"), Wideband Code Division Multiple Access ("WCDMA"), Enhanced Data GSM Environment ("EDGE"), International Mobile Telecommunications-2000 ("IMT-2000"), Digital Enhanced Cordless Telecommunications ("DECT"), etc., as well as to other network services that shall become available in time. In this regard, the techniques of the invention may be applied independently of the method of data transport, and does not depend on any particular network architecture, or underlying protocols.

Figure 2A:
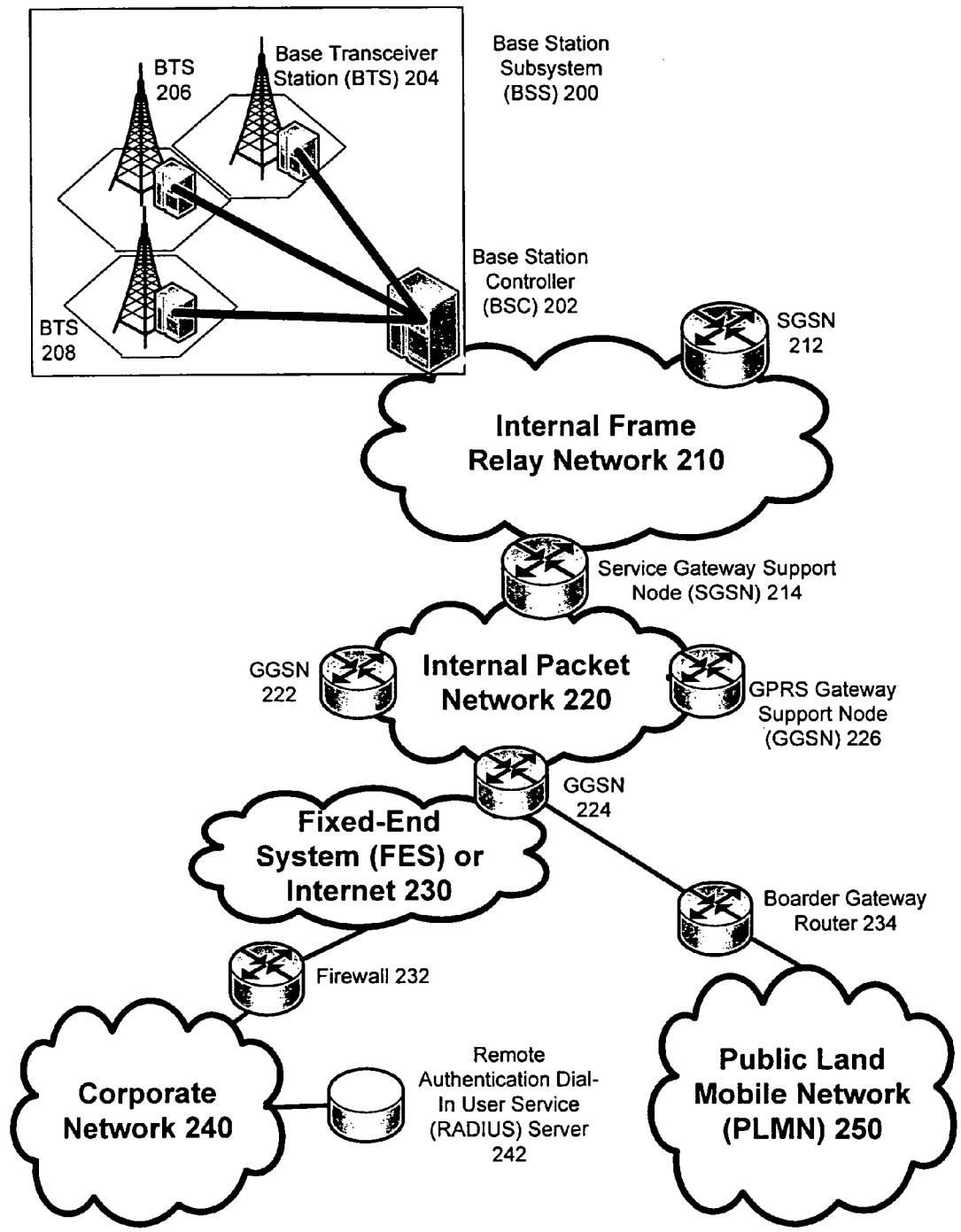
FIG. 2A illustrates an overview of a network environment suitable for service by embodiments of the invention.

FIG. 2A depicts an overall block diagram of an exemplary packet-based mobile cellular network environment, such as a GPRS network, in which the invention may be practiced. In such an environment, there are a plurality of Base Station Subsystems ("BSS") 200 (only one is shown), each of which comprises a Base Station Controller ("BSC") 202 serving a plurality of Base Transceiver Stations ("BTS") such as BTSs 204, 206, and 208. BTSs 204, 206, 208, etc. are the access points where users of packet-based mobile devices become connected to the wireless network. In exemplary fashion, the packet traffic originating from user devices is transported over the air interface to a BTS 208, and from the BTS 208 to the BSC 202. Base station subsystems, such as BSS 200, are a part of internal frame relay network 210 that may include Service GPRS Support Nodes ("SGSN") such as SGSN 212 and 214. Each SGSN is in turn connected to an internal packet network 220 through which a SGSN 212, 214, etc. can route data packets to and from a plurality of gateway GPRS support nodes (GGSN) 222, 224, 226, etc. As illustrated, SGSN 214 and GGSNs 222, 224, and 226 are part of internal packet network 220. Gateway GPRS serving nodes 222, 224 and 226 mainly provide an interface to external Internet Protocol ("IP") networks such as Public Land Mobile Network ("PLMN") 250, corporate intranets 240, or Fixed-End System ("FES") or the public Internet 230. As illustrated, subscriber corporate network 240 may be connected to GGSN 224 via firewall 232; and PLMN 250 is connected to GGSN 224 via boarder gateway router 234. The Remote Authentication Dial-In User Service ("RADIUS") server 242 may be used for caller authentication when a user of a mobile cellular device calls corporate network 240.

Generally, there can be four different cell sizes in a GSM network—macro, micro, pico and umbrella cells. The coverage area of each cell is different in different environments. Macro cells can be regarded as cells where the base station antenna is installed in a mast or a building above average roof top level. Micro cells are cells whose antenna height is under average roof top level; they are typically used in urban areas. Pico cells are small cells having a diameter is a few dozen meters; they are mainly used indoors. On the other hand, umbrella cells are used to cover shadowed regions of smaller cells and fill in gaps in coverage between those cells.

Figure 2B:
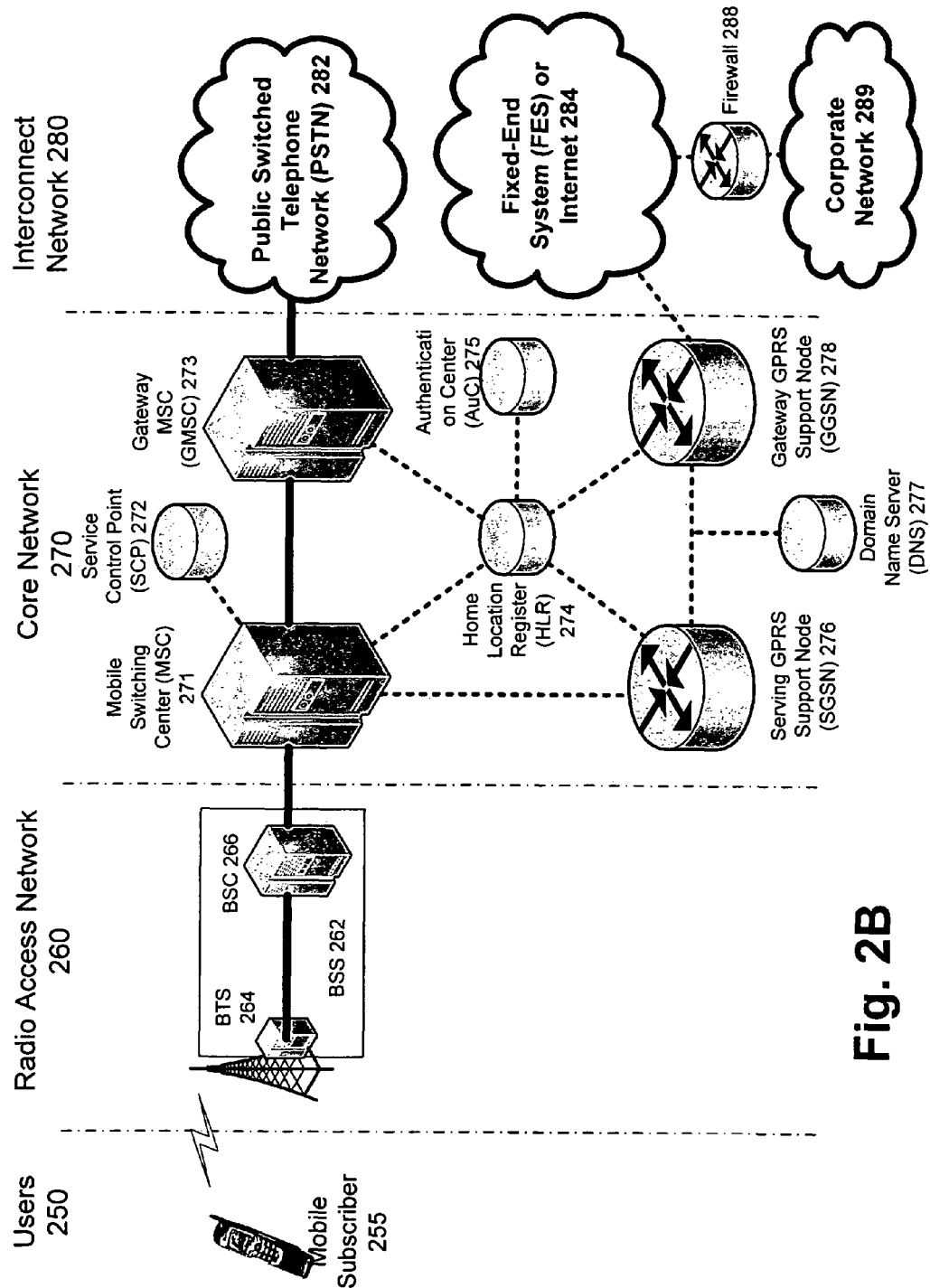
FIG. 2B illustrates a GPRS network architecture that may incorporate various aspects of the invention.

FIG. 2B illustrates the architecture of a typical GPRS network as segmented into four groups: users 250, radio access network 260, core network 270, and interconnect network 280. Users 250 comprise a plurality of end users (though only mobile subscriber 255 is shown in FIG. 2B). Radio access network 260 comprises a plurality of base station subsystems such as BSSs 262, which include BTSs 264 and BSCs 266. Core network 270 comprises a host of various network elements. As illustrated here, core network 270 may comprise Mobile Switching Center ("MSC") 271, Service Control Point ("SCP") 272, gateway MSC 273, SGSN 276, Home Location Register ("HLR") 274, Authentication Center ("AuC") 275, Domain Name Server ("DNS") 277, and GGSN 278. Interconnect network 280 also comprises a host of various networks and other network elements. As illustrated in FIG. 2B, interconnect network 280 comprises Public Switched Telephone Network ("PSTN") 282, Fixed-End System ("FES") or Internet 284, firewall 288, and Corporate Network 289.

A mobile switching center can be connected to a large number of base station controllers. At MSC 271, for instance, depending on the type of traffic, the traffic may be separated in that voice may be sent to Public Switched Telephone Network ("PSTN") 282 through Gateway MSC ("GMSC") 273, and/or data may be sent to SGSN 276, which then sends the data traffic to GGSN 278 for further forwarding.

When MSC 271 receives call traffic, for example, from BSC 266, it sends a query to a database hosted by SCP 272. The SCP 272 processes the request and issues a response to MSC 271 so that it may continue call processing as appropriate.

The HLR 274 is a centralized database for users to register to the GPRS network. HLR 274 stores static information about the subscribers such as the International Mobile Subscriber Identity ("IMSI"), subscribed services, and a key for authenticating the subscriber. HLR 274 also stores dynamic subscriber information such as the current location of the mobile subscriber. Associated with HLR 274 is AuC 275. AuC 275 is a database that contains the algorithms for authenticating subscribers and includes the associated keys for encryption to safeguard the user input for authentication.

In the following, depending on context, the term "mobile subscriber" sometimes refers either to the end user and sometimes to the actual portable device used by an end user of the mobile cellular service. When a mobile subscriber turns on his or her mobile device, the mobile device goes through an attach process by which the mobile device attaches to an SGSN of the GPRS network. In FIG. 2B, when mobile subscriber 255 initiates the attach process by turning on the network capabilities of the mobile device, an attach request is sent by mobile subscriber 255 to SGSN 276. The SGSN 276 queries another SGSN, to which mobile subscriber 255 was attached before, for the identity of mobile subscriber 255. Upon receiving the identity of mobile subscriber 255 from the other SGSN, SGSN 276 requests more information from mobile subscriber 255. This information is used to authenticate mobile subscriber 255 to SGSN 276 by HLR 274. Once verified, SGSN 276 sends a location update to HLR 274 indicating the change of location to a new SGSN, in this case SGSN 276. HLR 274 notifies the old SGSN, to which mobile subscriber 255 was attached before, to cancel the location process for mobile subscriber 255. HLR 274 then notifies SGSN 276 that the location update has been performed. At this time, SGSN 276 sends an Attach Accept message to mobile subscriber 255, which in turn sends an Attach Complete message to SGSN 276.

After attaching itself with the network, mobile subscriber 255 then goes through the authentication process. In the authentication process, SGSN 276 sends the authentication information to HLR 274, which sends information back to SGSN 276 based on the user profile that was part of the user's initial setup. The SGSN 276 then sends a request for authentication and ciphering to mobile subscriber 255. The mobile subscriber 255 uses an algorithm to send the user identification (ID) and password to SGSN 276. The SGSN 276 uses the same algorithm and compares the result. If a match occurs, SGSN 276 authenticates mobile subscriber 255.

Next, the mobile subscriber 255 establishes a user session with the destination network, corporate network 289, by going through a Packet Data Protocol ("PDP") activation process. Briefly, in the process, mobile subscriber 255 requests access to the Access Point Name ("APN"), for example, UPS.com (e.g., which can be corporate network 279 in FIG. 3) and SGSN 276 receives the activation request from mobile subscriber 255. SGSN 276 then initiates a Domain Name Service ("DNS") query to learn which GGSN node has access to the UPS.com APN. The DNS query is sent to the DNS server within the core network 270, such as DNS 277, which is provisioned to map to one or more GGSN nodes in the core network 270. Based on the APN, the mapped GGSN 278 can access the requested corporate network 279. The SGSN 276 then sends to GGSN 278 a Create Packet Data Protocol ("PDP") Context Request message that contains necessary information. The GGSN 278 sends a Create PDP Context Response message to SGSN 276, which then sends an Activate PDP Context Accept message to mobile subscriber 255.

Once activated, data packets of the call made by mobile subscriber 255 can then go through radio access network 260, core network 270, and interconnect network 280, in particular fixed-end system or Internet 284 and firewall 288, to reach corporate network 289.

Thus, network elements that may implicate the functionality of the health reporting collection and reporting in accordance with the invention may include but are not limited to Gateway GPRS Support Node tables, Fixed End System router tables, firewall systems, VPN tunnels, and any number of other network elements as required by the particular digital network.

Figure 2C:
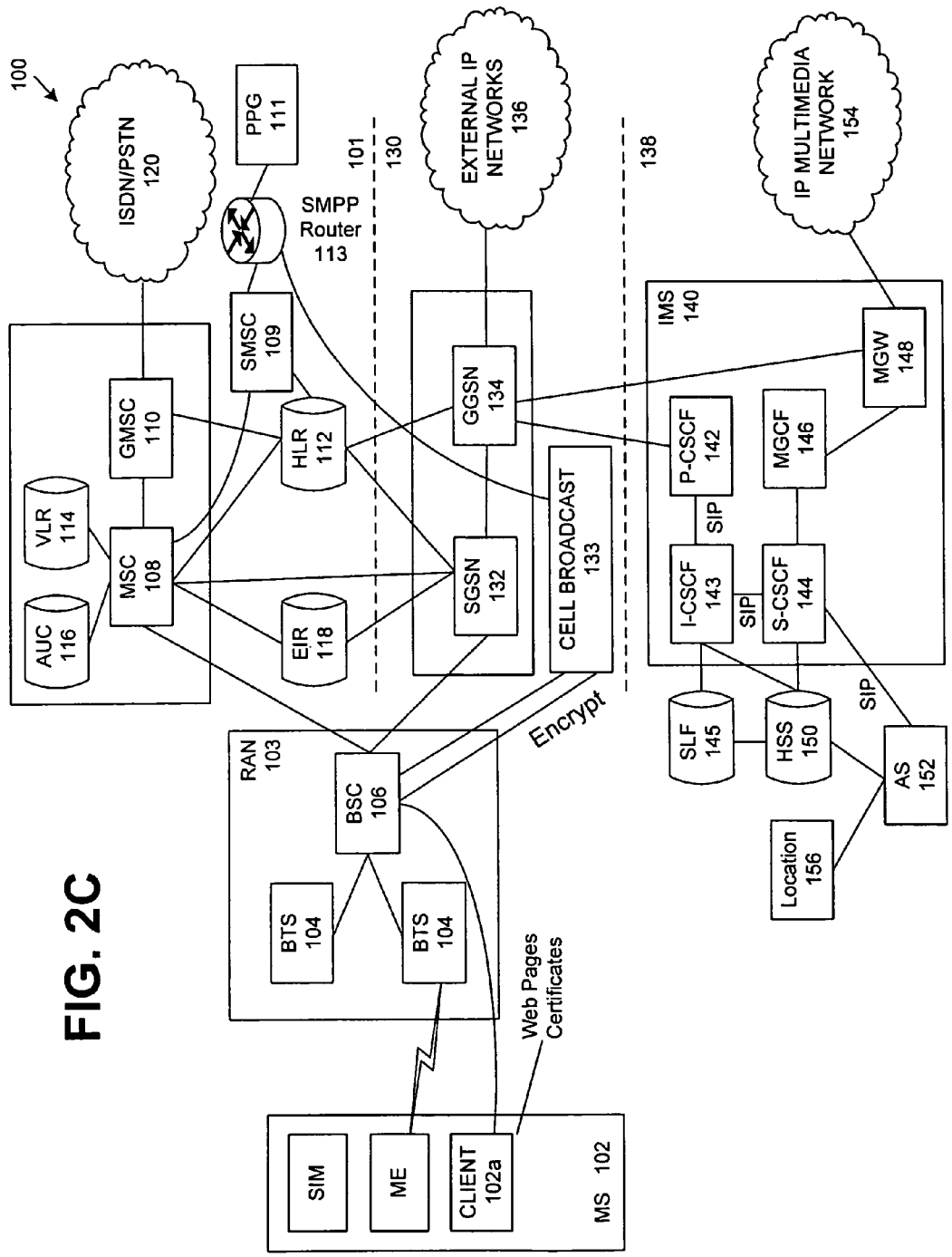
FIG. 2C illustrates an alternate block diagram of an exemplary GSM/GPRS/IP multimedia network architecture in which the invention may be employed.

FIG. 2C shows another exemplary block diagram view of a GSM/GPRS/IP multimedia network architecture 100 in which the health condition data collection and reporting of the present invention may be incorporated. As illustrated, architecture 100 of FIG. 2C includes a GSM core network 101, a GPRS network 130 and an IP multimedia network 138. The GSM core network 101 includes a Mobile Station (MS) 102, at least one Base Transceiver Station (BTS) 104 and a Base Station Controller (BSC) 106. The MS 102 is physical equipment or Mobile Equipment (ME), such as a mobile phone or a laptop computer that is used by mobile subscribers, with a Subscriber identity Module (SIM). The SIM includes an International Mobile Subscriber Identity (IMSI), which is a unique identifier of a subscriber. The BTS 104 is physical equipment, such as a radio tower, that enables a radio interface to communicate with the MS. Each BTS may serve more than one MS. The BSC 106 manages radio resources, including the BTS. The BSC may be connected to several BTSs. The BSC and BTS components, in combination, are generally referred to as a base station (BSS) or radio access network (RAN) 103.

The GSM core network 101 also includes a Mobile Switching Center (MSC) 108, a Gateway Mobile Switching Center (GMSC) 110, a Home Location Register (HLR) 112, Visitor Location Register (VLR) 114, an Authentication Center (AuC) 118, and an Equipment Identity Register (EIR) 116. The MSC 108 performs a switching function for the network. The MSC also performs other functions, such as registration, authentication, location updating, handovers, and call routing. The GMSC 110 provides a gateway between the GSM network and other networks, such as an Integrated Services Digital Network (ISDN) or Public Switched Telephone Networks (PSTNs) 120. In other words, the GMSC 110 provides interworking functionality with external networks.

The HLR 112 is a database that contains administrative information regarding each subscriber registered in a corresponding GSM network. The HLR 112 also contains the current location of each MS. The VLR 114 is a database that contains selected administrative information from the HLR 112. The VLR contains information necessary for call control and provision of subscribed services for each MS currently located in a geographical area controlled by the VLR. The HLR 112 and the VLR 114, together with the MSC 108, provide the call routing and roaming capabilities of GSM.

The AuC 116 provides the parameters needed for authentication and encryption functions. Such parameters allow verification of a subscriber's identity. The EIR 118 stores security-sensitive information about the mobile equipment.

A Short Message Service Center (SMSC) 109 allows one-to-one Short Message Service (SMS) messages to be sent to/from the MS 102. A Push Proxy Gateway (PPG) 111 is used to "push" (i.e., send without a synchronous request) content to the MS 102. The PPG 111 acts as a proxy between wired and wireless networks to facilitate pushing of data to the MS 102. A Short Message Peer to Peer (SMPP) protocol router 113 is provided to convert SMS-based SMPP messages to cell broadcast messages. SMPP is a protocol for exchanging SMS messages between SMS peer entities such as short message service centers. It is often used to allow third parties, e.g., content suppliers such as news organizations, to submit bulk messages.

To gain access to GSM services, such as speech, data, and short message service (SMS), the MS first registers with the network to indicate its current location by performing a location update and IMSI attach procedure. The MS 102 sends a location update including its current location information to the MSC/VLR, via the BTS 104 and the BSC 106. The location information is then sent to the MS's HLR. The HLR is updated with the location information received from the MSC/VLR. The location update also is performed when the MS moves to a new location area. Typically, the location update is periodically performed to update the database as location updating events occur.

The GPRS network 130 is logically implemented on the GSM core network architecture by introducing two packet-switching network nodes, a serving GPRS support node (SGSN) 132, a cell broadcast and a Gateway GPRS support node (GGSN) 134. The SGSN 132 is at the same hierarchical level as the MSC 108 in the GSM network. The SGSN controls the connection between the GPRS network and the MS 102. The SGSN also keeps track of individual MS's locations and security functions and access controls.

A Cell Broadcast Center (CBC) 133 communicates cell broadcast messages that are typically delivered to multiple users in a specified area. Cell Broadcast is one-to-many geographically focused service. It enables messages to be communicated to multiple mobile phone customers who are located within a given part of its network coverage area at the time the message is broadcast.

The GGSN 134 provides a gateway between the GPRS network and a public packet network (PDN) or other IP networks 136. That is, the GGSN provides interworking functionality with external networks, and sets up a logical link to the MS through the SGSN. When packet-switched data leaves the GPRS network, it is transferred to an external TCP-IP network 136, such as an X.25 network or the Internet. In order to access GPRS services, the MS first attaches itself to the GPRS network by performing an attach procedure. The MS then activates a packet data protocol (PDP) context, thus activating a packet communication session between the MS, the SGSN, and the GGSN.

In a GSM/GPRS network, GPRS services and GSM services can be used in parallel. The MS can operate in one three classes: class A, class B, and class C. A class A MS can attach to the network for both GPRS services and GSM services simultaneously. A class A MS also supports simultaneous operation of GPRS services and GSM services. For example, class A mobiles can receive GSM voice/data/SMS calls and GPRS data calls at the same time.

A class B MS can attach to the network for both GPRS services and GSM services simultaneously. However, a class B MS does not support simultaneous operation of the GPRS services and GSM services. That is, a class B MS can only use one of the two services at a given time.

A class C MS can attach for only one of the GPRS services and GSM services at a time. Simultaneous attachment and operation of GPRS services and GSM services is not possible with a class C MS.

A GPRS network 130 can be designed to operate in three network operation modes (NOM1, NOM2 and NOM3). A network operation mode of a GPRS network is indicated by a parameter in system information messages transmitted within a cell. The system information messages dictates a MS where to listen for paging messages and how signal towards the network. The network operation mode represents the capabilities of the GPRS network. In a NOM1 network, a MS can receive pages from a circuit switched domain (voice call) when engaged in a data call. The MS can suspend the data call or take both simultaneously, depending on the ability of the MS. In a NOM2 network, a MS may not received pages from a circuit switched domain when engaged in a data call, since the MS is receiving data and is not listening to a paging channel In a NOM3 network, a MS can monitor pages for a circuit switched network while received data and vise versa.

The IP multimedia network 138 was introduced with 3GPP Release 5, and includes an IP multimedia subsystem (IMS) 140 to provide rich multimedia services to end users. A representative set of the network entities within the IMS 140 are a call/session control function (CSCF), a media gateway control function (MGCF) 146, a media gateway (MGW) 148, and a master subscriber database, called a home subscriber server (HSS) 150. The HSS 150 may be common to the GSM network 101, the GPRS network 130 as well as the IP multimedia network 138.

The IP multimedia system 140 is built around the call/session control function, of which there are three types: an interrogating CSCF (I-CSCF) 143, a proxy CSCF (P-CSCF) 142, and a serving CSCF (S-CSCF) 144. The P-CSCF 142 is the MS's first point of contact with the IMS 140. The P-CSCF 142 forwards session initiation protocol (SIP) messages received from the MS to an SIP server in a home network (and vice versa) of the MS. The P-CSCF 142 may also modify an outgoing request according to a set of rules defined by the network operator (for example, address analysis and potential modification).

The I-CSCF 143, forms an entrance to a home network and hides the inner topology of the home network from other networks and provides flexibility for selecting an S-CSCF. The I-CSCF 143 may contact a subscriber location function (SLF) 145 to determine which HSS 150 to use for the particular subscriber, if multiple HSS's 150 are present. The S-CSCF 144 performs the session control services for the MS 102. This includes routing originating sessions to external networks and routing terminating sessions to visited networks. The S-CSCF 144 also decides whether an application server (AS) 152 is required to receive information on an incoming SIP session request to ensure appropriate service handling. This decision is based on information received from the HSS 150 (or other sources, such as an application server 152). The AS 152 also communicates to a location server 156 (e.g., a Gateway Mobile Location Center (GMLC)) that provides a position (e.g., latitude/longitude coordinates) of the MS 102.

The HSS 150 contains a subscriber profile and keeps track of which core network node is currently handling the subscriber. It also supports subscriber authentication and authorization functions (AAA). In networks with more than one HSS 150, a subscriber location function provides information on the HSS 150 that contains the profile of a given subscriber.

The MGCF 146 provides interworking functionality between SIP session control signaling from the IMS 140 and ISUP/BICC call control signaling from the external GSTN networks (not shown). It also controls the media gateway (MGW) 148 that provides user-plane interworking functionality (e.g., converting between AMR- and PCM-coded voice). The MGW 148 also communicates with other IP multimedia networks 154.

Push to Talk over Cellular (PoC) capable mobile phones register with the wireless network when the phones are in a predefined area (e.g., job site, etc.). When the mobile phones leave the area, they register with the network in their new location as being outside the predefined area. This registration, however, does not indicate the actual physical location of the mobile phones, but in accordance with the invention, the predefined area can be associated with a nearby BTS such that health reporting data can be messaged to devices in the pre-defined area.

Wireless Wide Area Network (WWAN) Health Data Collection and Reporting Services

As discussed in the background, people interested in learning about their own health conditions relating to a particular condition historically have had few options. While individual medical institutions maintain their own electronic records, an average health services consumer interested in his or her own health data and conditions cannot access their own health information in real-time. Existing health data measurement devices may present accurate real-time data about a user's current health, but the locality of the data prevents it from making a further impact. A user must in effect then interpret and make any decisions about the data before initiating any further steps.

Accordingly, the invention provides systems and methods for reporting health condition data with improved reliability and relevancy, fast access to the data, and with historical memory of a user's health. In various embodiments, the invention communicatively couples existing medical devices and features to network enabled portable devices, such as wireless phones, and provides services, interfaces and agents for achieving an exchange with a health station server of a user's health data that is measured by the medical devices.

As illustrated in FIG. 1A, the architectural framework for various embodiments of the invention includes a health measuring device HMD paired with a portable device PD, as illustrated by the dashed oval. Health measuring device HMD can be any health measuring device, existing today or developed in the future, whether provided as a standalone or incorporated into other devices (e.g. a watch), and thus, its exemplary appearance in FIG. 1A shall thus not be taken as a resemblance to any particular medical device, nor shall it be considered to be limiting on the scope of medical devices contemplated for pairing with a portable device in accordance with the invention. In accordance with various embodiments described herein, the invention includes transmitting health data measured by the health measuring device HMD via interfaces of the portable device PD, including any pre-processing of the health data performed by the portable device PD, to a health station node HSN via a wireless wide area network WWAN, which stores the health data, enabling a set of advantageous scenarios described below.

The invention may also be implemented to attempt to send the health data to the health station node HSN via alternate wide area networks (not shown), e.g., other wireless wide area networks, the Internet, etc. In such embodiments, the invention thus may provide multi-vendor interoperability in case, for instance, the wireless wide area network WWAN lacks coverage for the user's device or is down, and thus allows the health data, which might be critical, to nonetheless reach the health station node HSN by alternate means (e.g., roaming, TCP/IP channel, etc.).

Figure 1B:
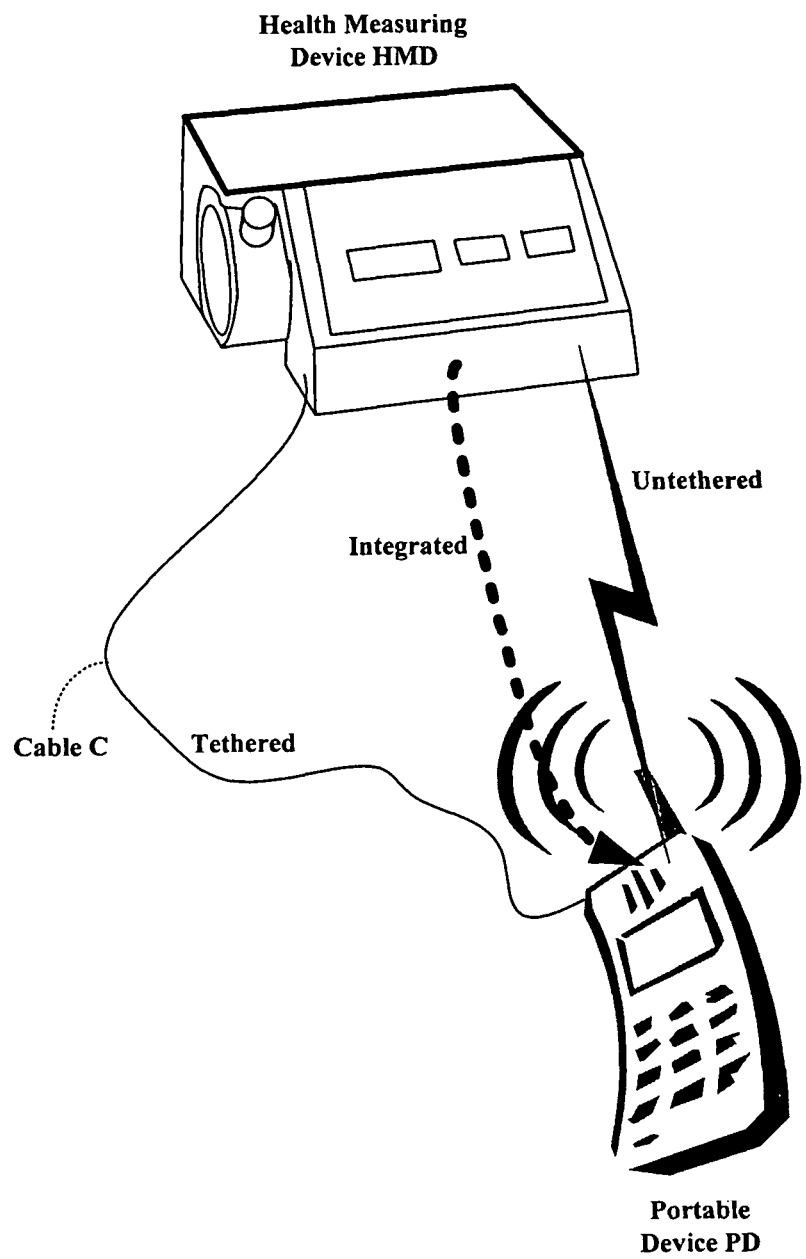
FIG. 1B illustrates exemplary ways that a health data measuring device may be paired with a portable device in various exemplary, non-limiting embodiments of the invention.

As illustrated in FIG. 1B, the medical device HMD may be communicatively coupled to the portable device PD via a traditional cable interface C, such as USB (tethered), via wireless means, such as Bluetooth (untethered) or the medical device may itself be integrated into the portable device (integrated), as shown conceptually by the dashed arrow implicating that the medical device HMD is incorporated into the handset design of the portable device PD as a single integrated device. Again, no limitation on the scope of medical devices HMD is intended by its exemplary non-limiting appearance in the illustration of FIG. 1B.

For an exemplary, non-exhaustive list of medical devices that may be communicatively coupled to a computing device in accordance with the invention, medical devices that measure health data include, but are not limited to, heart rate monitors, pulse monitors, blood pressure monitors, EKG/ECG monitors, EEG monitors, temperature monitors (e.g., thermometers), blood sugar level monitors, pH level monitors, perspiration monitors, breathalyzers, exercise monitors, neural activity monitors, and any device that measures a signal from a condition relating to the health of an individual entity. Other health measuring instruments, now or later developed, which may reasonably be communicatively coupled to (such as attached to, achieve wireless communications with, or be integrated with) portable devices should be apparent to those in the medical device arts as well, and accordingly this list should be considered exemplary, and non-exhaustive.

The invention thus interoperates medical devices with wireless technologies and terminals, allowing a host of scenarios that are not otherwise possible. For instance, automatic alerts can be extended to health professionals in the event of a significant risk, as may be detected from a pattern found in a current set of health data, or in a historical set of health data. In the case of an emergency detected with respect to a user's current health condition (such as dangerously low blood sugar levels for a diabetic), the invention enables ambulance drivers and other emergency workers a chance to reach a person faster.

For another example, a user is training for a marathon having a portable device with a heart rate monitor. The user wishes to see the past 6 months of data showing average heart rate over the time period as a graph. The user also wishes to send that data to a family member (maybe to impress them with hard training), or to a concerned family doctor (who may think there is risk of heart failure). Accordingly, the user requests the data with a user interface of the portable device, a request is made to the health station server of the invention upon connection with the network, and a graph is formulated in accordance with the user's request and delivered to the user for display on the portable device. Similarly, the user can direct that the graph data be delivered to the family member's portable device, e.g., phone, or to the family doctor's portable device. The user can also direct that the graph data be delivered to an email address, or be posted to a user health data site, where authorized third parties may view designated user health data.

For example, in an embodiment of the invention where a heart rate monitor is communicatively coupled (tethered, wireless, or integrated) to a user's portable device, e.g., cell phone, a user's heart rate can be continuously measured by the heart rate monitor and can be continuously received by the portable device. In accordance with settings for the health service of the invention, the handset sends measurements, e.g., periodically, to a Medical Server Unit MSU. The Medical Server Unit MSU receives the measurements and compares the measurements to the subscriber's database for health monitoring advices. If any measurement limits are surpassed, or if a bad health condition is detected as a pattern in the historical health data for the user, the Medical Server Unit sends an alert, e.g., to a call center where health professionals can become involved.

An optional Emergency button can also be included on any medical device according to standard interfacing enabled by the invention, or incorporated into the portable device itself, to indicate a pre-specified kind of Emergency. For instance, a diabetic can pre-specify that the Emergency button will initiate a notification any time blood sugar levels fall below a predetermined point. In this regard, while health alert buttons exist as closed systems, there are no commercially available pairings of medical devices with WWAN enabled portable devices that provide connectivity to a Medical surveillance system.

In addition, due to end to end integration of a WWAN health station server with a portable device and health measuring device in accordance with the architecture of the invention, software updates to health measuring devices can be achieved via a standard set of interfaces for medical devices communicatively coupled to portable devices without the need to replace, or purchase a new, health measuring device.

Accordingly, the invention enables versatility of medical devices and connectivity of medical devices to health services through a portable device, such as a mobile phone. The health services of the invention are particularly advantageous for those with disabilities, as well as for health professionals, and health watch organizations, which are all afforded additional opportunities to make use of health condition data that is collected according to the invention, though the invention is not limited to such uses of the health station server of the invention. In exemplary non-limiting embodiments, the invention uses control channels, such as RF control channels, or the data network to send specific periodic medical measurements to one or more health storage devices on the network, aggregating the user's data at a health data server. On the network side, in one embodiment, the health data server is provided as an additional node of the network that monitors measurements for a user, and sends an alert protocol to a call center if an activity, such as an anomaly, is detected concerning the user's data.

In this regard, herein, an "activity" refers to a physiological process of a biological entity, such as the user. In this respect, the invention may be applied to "users" that are not human beings. For instance, the invention may be applied to determine whether a plant is receiving has a health condition (e.g., not receiving enough water, has a plant disease, for instance, as might be determined by image processing algorithms that detect spots, leaf color, or the like).

For embodiments where health professionals, third parties or the like are sent alerts of such an activity concerning a user's health data, the methods of the invention may include applying a set of robust criteria that detect likely false alarms before notifying any third party. Upon detection, false alarms can be filtered out or forwarded to certain third parties anyway. In this way, for instance, monitoring an ongoing activity can help a concerned parent to monitor the health of a child for a critical condition, but the concerned parent will not be concerned with false alarms (e.g., a pre-specified set of aberrations in the data). Thus, for instance, a child may stumble on some stairs causing a glitch (false alarm) in the data that is not serious (not detected by the method), but if Mom is set up to be notified for false alarms, Mom can always come to a rescue with a bandage.

Alternatively, a user may wish to see the last 6 month's of heart rate data, e.g., to compare the user's heart rate information for a period of jogging against the user's heart rate information for a period of no exercise. Thus, while the invention may particularly be advantageous with respect to certain emergency health scenarios, the invention may also be applicable to an end user's curiosity about his or her health data. For instance, a device that measures perspiration over time for a user may be communicatively coupled to a portable device in accordance with the invention. In such a case, if a user reported perspiration data to the health data server of the invention for a period of 1 year, the user could examine averages, and correlate peaks and valleys to times during the day in which a user is likely to perspire. To the extent that perspiration is tied to stress levels, a user may be able to identify high risk stressful moments that recur in their lives, and attempt to modify their behavior to avoid them. Because the historical record stored by the health data server is recorded without intrusively involving the user, i.e., since the reporting can be automatically and/or periodically achieved without involving the user, a variety of "curiosity" scenarios emerge. A person might not pay hundreds of dollars for the information, but that does not mean that the person would not be interested in the information if it was otherwise made available, in a way that is easy to achieve via a simple request and also user customizable for display.

In this regard, the health data collection and reporting services of the present invention enable a broad health data service for the wireless wide area network ("WWAN") industry, involving components for both the network side (servers, software and storage) and the device side (medical device integration, software and interfaces).

Figure 3A:
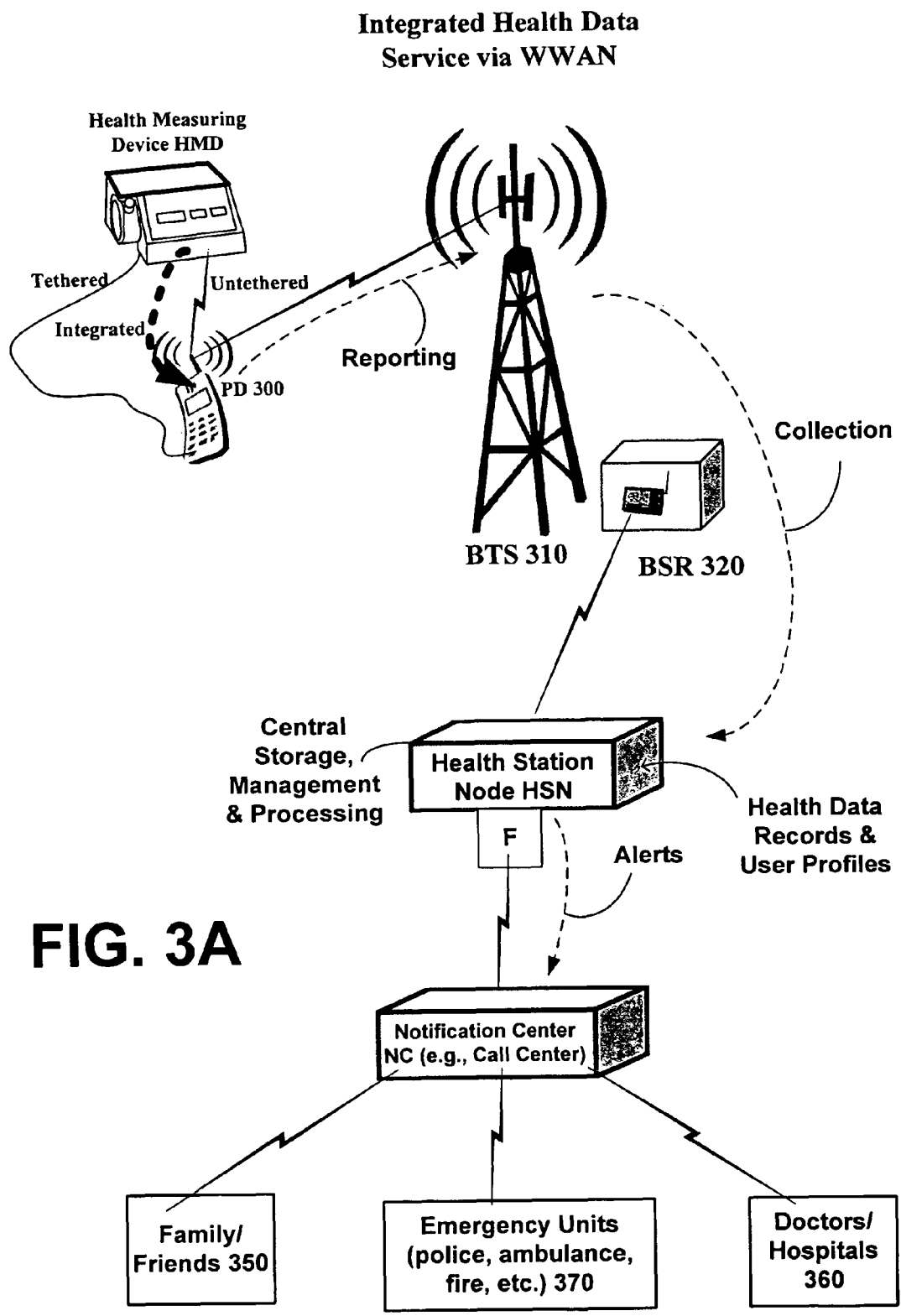
FIGS. 3A to 3C are block diagrams illustrating various exemplary, non-limiting aspects of a WWAN health station and services architecture in accordance with the present invention.
Figure 3B:
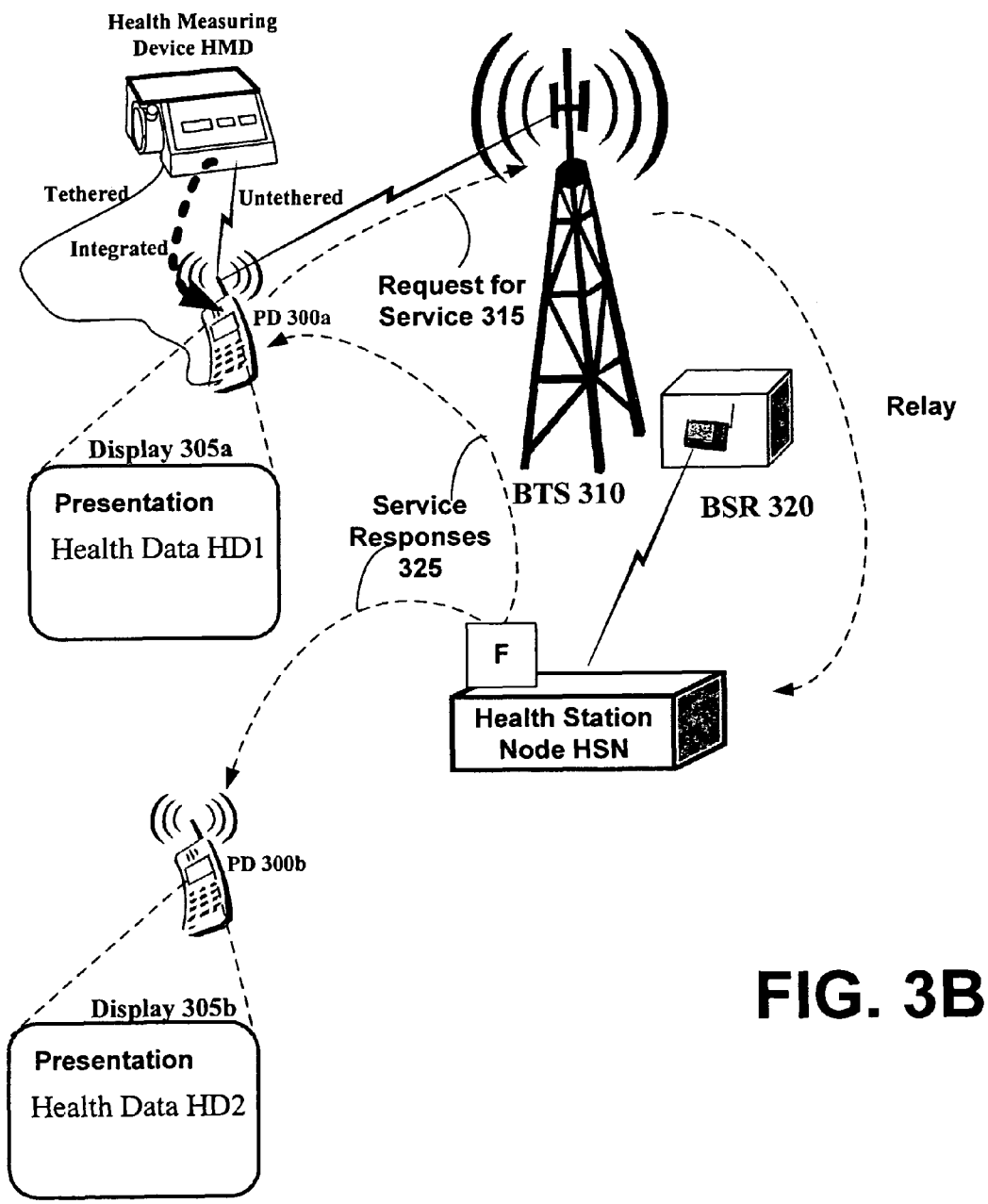
Figure 3C:
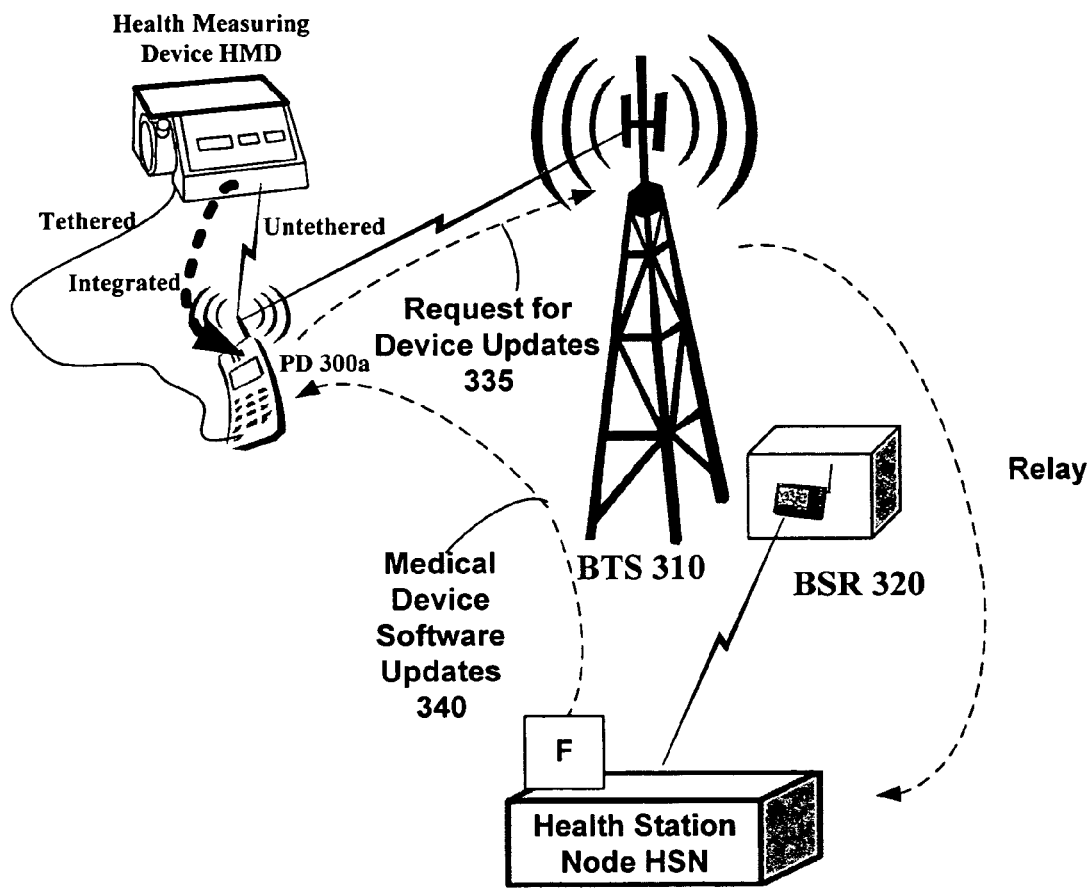

FIGS. 3A to 3C are block diagrams illustrating various exemplary, non-limiting aspects of a WWAN health station and services architecture in accordance with the present invention. As shown in FIG. 3A, a health measuring device HMD is communicatively coupled to a portable device 300 via interfaces provided in accordance with the invention, which provide a standard way for any health measuring device to be incorporated into the health data services framework of the invention. The health measuring device HMD measure's data from a user, e.g., from a user's blood, skin, heart beat, etc., and reports that data to a health station node HSN located on the network for central storage, management and processing of health data. The health station node may include a plurality of computing devices and storage devices, located in the same or disparate locations, as the case may be.

The health data from the health measuring device HMD is transmitted to the WWAN including base transceiver stations BTSs 310, having base station rooms BSRs 320 for housing certain apparatus associated with BTSs 310. One or more intermediate computing or storage devices can be included in or around BTSs 310 or BSRs 320 in order to store certain health data prior to forwarding the health data to the health station node HSN. For instance, where non-critical health data is involved, the transmission of health data can be relegated to a background network process to prioritize more important data transmissions depending on network bandwidth. Once the health data records are formed, and associated with user profiles, a variety of health data services can be enabled for users. For instance, as shown in FIG. 3A, based on filters F for a user profile, pre-determined sets of health data (such as those that trigger emergency circumstances) can be designed to trigger an alert to a notification center NC, which can then further involve family/friends 350, emergency units 370, or health professionals 360. The notification center NC can be a separate call center, for instance, though the notification center NC of the invention need not be a separate component from health station node HSN. As a result, a diabetic user, for instance, can instantaneously spring health professionals to action if a critically low blood sugar level is detected by pre-configuring the account to observe for such levels.

FIG. 3B illustrates another scenario enabled by the invention. In this regard, with access to a user's health data via the health data services offered by health station node HSN, a user can request a certain presentation of data (e.g., statistical data, such as averages) of a certain health condition or measurement over a selected date range by making a request for service 315 via the user interface off the portable device 300a. Through the WWAN, the health station node HSN receives the request, performs any optional authentication of the device and/or user, and then processes the data to service the request. If the request includes a request to display data on the user's portable device 300a, then the health station node HSN delivers the health data to the user's display 305a of the portable device 300a via response 325. In this fashion, a user has real-time access to his or her historical health data, and can make comparisons over time, via the health data services of the invention. The service responses can be pre-filtered via filters F prior to delivery of the response according to any pre-configured restrictions on such health data for the user.

In addition, the request may be to display certain health data on another user's portable device. Thus, for instance, one response 325 may be to display certain requested health condition data on a friend's or a doctor's portable device 300b, in which case the health condition data appears on the friends' or doctor's display 305b of their portable device 300b. In this fashion, the data can be customized for an expert, such as a doctor, which might be different than the data that might be displayed to a non-expert, such as the user himself. One can thus begin to see the advantageous scenarios that emerge from empowering the user with his or her own health data via the health data services of the invention.

FIG. 3C illustrates yet another advantage of the architecture of the invention. In this regard, the health measuring devices HMD today are equipped with software in some cases that perform some of the functionality of the device HMD. In this respect, if significant updates to the software is made, today, a user must buy a new machine in the case of a standalone machine; however, with the invention, a software delivery framework is enabled for updates whereby the portable device 300a may make a request for device updates 335, which when received by health station node HSN, delivers the medical software updates 340 to the portable device 300a for installation on the portable device. In this fashion, a common framework is enabled to keep medical devices as up to date as possible.

Figure 4:
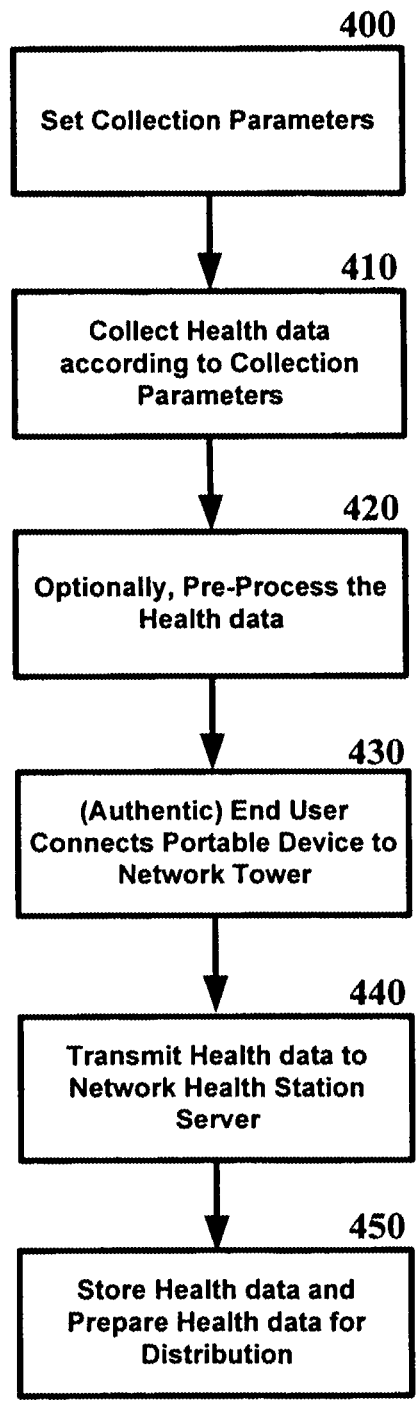
FIG. 4 is an exemplary non-limiting flow diagram showing the collection of health condition data of health condition data in a WWAN health station and services architecture of the present invention.

FIG. 4 is an exemplary non-limiting flow diagram showing the collection of health condition data in a WWAN health station and services architecture of the present invention. At 400, a user can pre-configure his or her account for health data services to adhere to certain collection parameters, e.g., that specify how often to transmit data, in what format, which data from the health measuring device to collect, etc. At 410, the health data is collected by the measuring device, and optionally pre-processed at 420 prior to transmission to the health data server. A variety of reasons may exist to pre-process the data, e.g., to format it according to communications protocols, to compress the data, to encrypt the data, to transform raw data into a more meaningful condition, etc. At 430, after any authentication is settled, the end user connects the portable device to the network, and at 440, the health data is transmitted to the health station server, directly or indirectly through one or more network intermediaries. Any known or later developed methods of authentication may be utilized in accordance with the invention to authenticate any one or more of a user, computing device of the user, a designated recipient of health data, or a computing device of such designated recipient.

Figure 5:
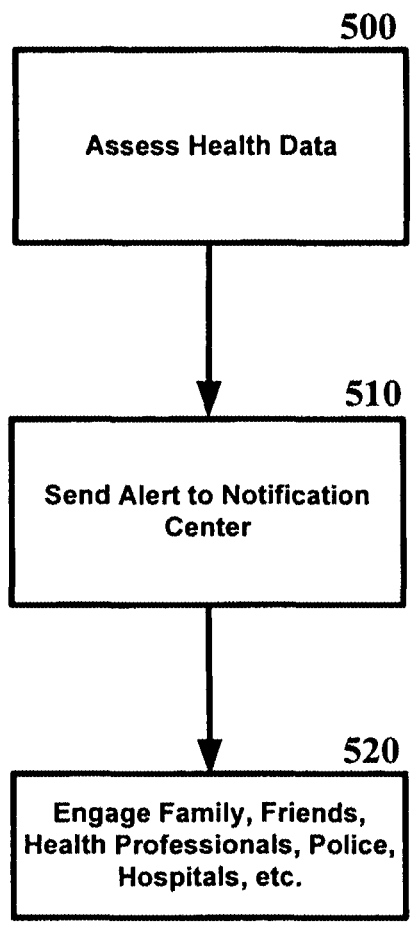
FIG. 5 is an exemplary non-limiting flow diagram showing the reporting of health condition data to one or more call centers in a WWAN health station and services architecture of the present invention.

FIG. 5 is an exemplary non-limiting flow diagram showing the reporting of health condition data to one or more call centers in a WWAN health station and services architecture of the present invention. Once the health station node has acquired a user's health data, the data may be assessed or analyzed as shown at 500 of FIG. 5. After analysis, at 510, if there is an alert condition found in the data, the alert can be sent to a notification center, such as a call center. The notification center, in turn, contacts the right set of people to help service the alert. For instance, the notification center may alert family, friends, health professionals, the police, ambulance drivers, etc. for speedy response to the emergency.

Figure 6:
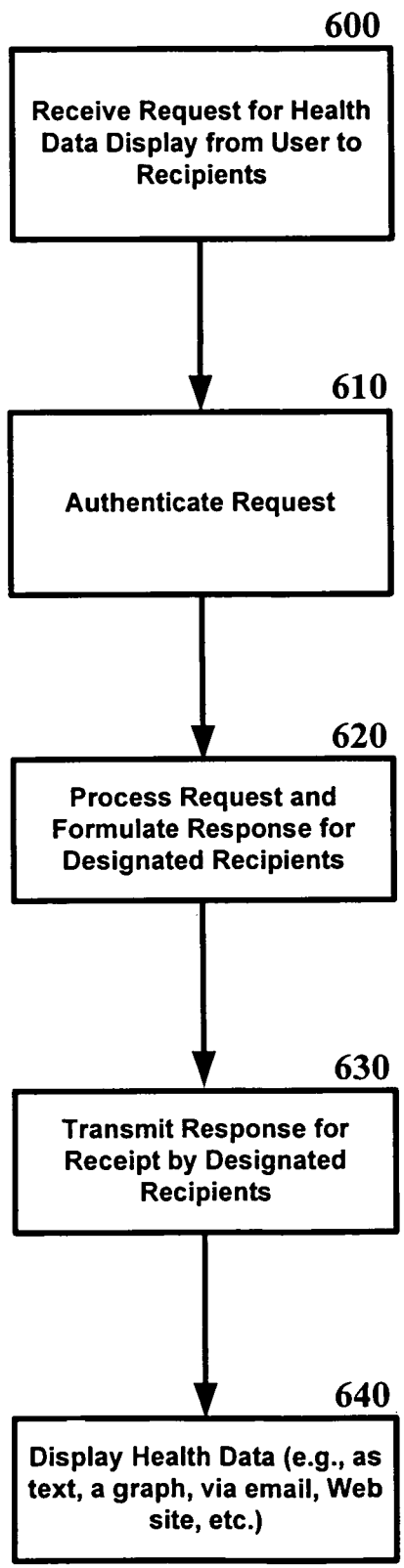
FIG. 6 is an exemplary non-limiting flow diagram showing the request for health data information by a user, and a corresponding response by a health station server in a WWAN health station and services architecture of the present invention.

FIG. 6 is an exemplary non-limiting flow diagram showing the request for health data information by a user, and a corresponding response by a health station server in a WWAN health station and services architecture of the present invention. Once the health station node has acquired a user's health data (e.g., see FIG. 4), at 600, a user may send a request to the health station node for some of the user's health data to be displayed for one or more recipients, which may include the user himself or herself. At 610, the device and/or user are authenticated in order to determine that the request is not an improper attempt to view sensitive user data. At 620, the health station node processes the request and formulates an appropriate response for the recipients designated by the user request. At 630, the response(s) so formulated are transmitted to the designated recipients. Finally, at 640, the health data is displayed; e.g., as text or a graph on display of the recipients' portable devices, or the recipients can be drawn to the information via an email, a link in an email to a Web site, or by allowing access to the user's health data through a Web site.

Any wireless means for delivering health condition data from a measuring device to a portable device, such as a phone, is considered for embodiments of the invention including Bluetooth, radio broadcast, etc. Also, health condition data can be transmitted from portable device to portable device in accordance with the invention as well.

Optionally, some pre-processing (data processing, compression, encryption, etc.) of the health data may be performed prior to being received by the health station node of the invention; otherwise, the health station node generally handles the aggregation, processing and management of the data on behalf of the user. While the health station node may be one or more servers and associated databases for storage of the health condition data, the health station node provides a centralized abstraction for collecting the tower health condition data in accordance with the invention.

In accordance with another aspect of the invention, a portable device with wireless communications capabilities, such as a mobile phone, PDA, blackberry device, handheld gaming system, portable media center, pager, etc., can receive one or more relevant pieces of health condition data according to one or more services.

In another embodiment, a separate GPS ("global positioning satellite") measurement can be recorded by PD 300, and the network can include such information alongside health condition data, such that in the event of an emergency, health professionals are instantly alerted to the location of the user.

The health condition data of the invention can be distributed to PD 300 via any available network channel, whether the control channel, the voice/data channel or a broadcast channel (e.g., for emergency storm warnings, and the like). Short message service (SMS) text messaging can also be utilized to deliver health condition data, such as emergency warnings. Thus, any requested health condition data from a portable device can be transmitted via a control channel, a voice channel, an SMS broadcast and/or a broadcast channel of the communications network so that the health condition data can be displayed.

Thus, in accordance with the invention, subscribers can access historical user health data measurements through a variety of wireless devices. Customers can be individual wireless subscribers, health report organizations, or national and educational organizations. For example, the WWAN health station services can be used as an alert system. Thus, independent of the request for services according to the invention that a user of a portable device can make, one can appreciate that the collection of data at the health station server on the network would make for an excellent repository of human research data for health conditions that could be mined for patterns, researched, etc. to the benefit of all, to form health maps, to create time elapsed videos; charts, graphs, etc.

While the present invention has been described in connection with the preferred embodiments of the various Figures, it is to be understood that other similar embodiments may be used or modifications and additions may be made to the described embodiment for performing the same function of the present invention without deviating therefrom. For example, one skilled in the art will recognize that the present invention as described in the present application may apply to any environment, whether wired or wireless, and may be applied to any number of such devices connected via a communications network and interacting across the network. For instance, the data from the health measuring instruments in accordance with the invention can be reported to the health station server of the invention via wired or wireless means, or a combination thereof. Therefore, the present invention should not be limited to any single embodiment, but rather should be construed in breadth and scope in accordance with the appended claims.

What is claimed:

1. A method, comprising:
configuring, via a mobile phone comprising a processor, a parameter of a health data service pertaining to a health associated with a subscriber identity, wherein the mobile phone is communicatively coupled to a health data measuring device;
receiving, by the mobile phone, health data related to the subscriber identity as recorded by the health data measuring device in accordance with the parameter;
in response to receiving the health data, directing, by the mobile phone, the health data to be sent from the mobile phone to a health data server that hosts the health data service and collectively stores and manages health information comprising the health data related to the subscriber identity;
forwarding, by the mobile phone, the health data to the health data server; and
transmitting, by the mobile phone, to the health data server, a request to present a subset of the health data on a second mobile phone associated with a non-medical identity, wherein, in response to the request, the health data server filters the health data to generate the subset of the health data and forwards the subset of the health data to the second mobile phone.

2. The method of claim 1, further comprising:
processing, by the mobile phone, the health data; and
generating, by the mobile phone, a notification related to a condition of the health associated with the subscriber identity in response to detecting a change regarding the health data as recorded by the health data measuring device.

3. The method of claim 1, further comprising:
processing, by the mobile phone, the health data; and
generating, by the mobile phone, contact information associated with a third mobile phone facilitating delivery of a notification, to the third mobile phone, of a condition related to the health associated with the subscriber identity in response to detecting a change regarding the health data as stored by the health data measuring device.

4. The method of claim 1, further comprising:
transmitting, by the mobile phone, a portion of the health data relating to a health-related event, wherein the portion of the health data facilitates detecting of a false positive indication of a specified activity in the health associated with the subscriber identity based on the portion of the health data, wherein the detecting comprises comparing the health data with a specified aberration associated with the portion of the health data, and wherein the aberration indicates the portion of the health data represents a false alarm.

5. The method of claim 1, further comprising:
requesting, by the mobile phone, forwarding of health-related data relating to the health data and pertaining to the subscriber identity stored by the health data server, via a network device of a wireless communications network, from the health data server to the mobile device;
receiving, by the mobile device, the health-related data; and
displaying, on the mobile device, the health-related data.

6. The method of claim 5, further comprising authenticating, by the mobile phone, the subscriber identity associated with the health-related data.

7. The method of claim 5, further comprising customizing, by the mobile phone, the health-related data to facilitate the displaying of the health-related data according to medical knowledge associated with a viewer identity determined for a viewer of the display.

8. The method of claim 5, wherein the receiving the health data comprises receiving the health data in a format facilitating the displaying of the health data as a graph on a display of the mobile phone.

9. The method of claim 5, wherein the receiving the health data comprises receiving, by the mobile phone, a uniform resource locator link identifying a location of the health data stored on the health data server.

10. The method of claim 1, further comprising:
requesting, by the mobile phone, from the health data server, a portion of the health information to be delivered to a designated recipient device, thereby directing the health data server to send the portion of the health information to the designated recipient device.

11. The method of claim 1, further comprising:
receiving, by the mobile phone, input information indicating actuation of an emergency button; and
in response to the input information being received, initiating, by the mobile phone, transmitting a message to the health data server, wherein, in response to receipt of the message at the health data server, an emergency response action is initiated.

12. The method according to claim 1, further comprising configuring, by the mobile phone, the processor of the mobile phone to perform an operation associated with the health data measuring device.

13. A mobile phone, comprising:
a memory to store executable instructions; and
a processor, coupled to the memory, that executes the executable instructions to perform operations comprising:
receiving health data related to a subscriber identity from a health measuring device;
transmitting the health data, via a network device of a wireless wide area network, to a health station server that hosts a health data service and collectively stores and manages health information comprising the health data;
transmitting a request to display a first portion of the health data on a second mobile phone associated with a non-medical identity, wherein, in response to the request, the health data server generates the first portion of the health data and forwards the first portion of the health data to the second mobile phone;
transmitting a request to display a second portion of the health data on a third mobile phone associated with the non-medical identity, wherein, in response to the request, the health data server generates the second portion of the health data and forwards the second portion of the health data to the third mobile phone; and
displaying a third portion of the health data, wherein the third portion of the health data is received from the health station server.

14. The mobile phone according to claim 13, wherein the health measuring device is a heart rate monitor.

15. The mobile phone according to claim 13, wherein the operations further comprise facilitating an operation of the health measuring device.

16. The mobile phone according to claim 13, wherein the health measuring device is attached to the mobile phone via a cable.

17. The mobile phone according to claim 13, wherein the health measuring device is communicatively coupled to the mobile phone via a wireless communication link.

18. A method, comprising:
receiving, by a system comprising a processor, health data related to a subscriber identity that is associated with a health data service hosted by the system and contact information relating to the health data, wherein the contact information comprises:
first contact information for a first contact identity associated with a first mobile phone, wherein the first mobile phone is communicatively coupled to a health data measuring device utilized to record the health data relating to a health associated with the subscriber identity,
second contact information for a second contact identity associated with a second mobile phone, wherein the second contact identity is determined to lack a defined level of medical proficiency, and
third contact information for a third contact identity associated with a third mobile phone, wherein the third contact identity is determined to have the defined level of medical proficiency;

receiving, by the system via the first mobile phone, the health data as recorded by the health measuring device;

storing, by the system, health information comprising the health data;

receiving, by the system, first input information relating to a first portion of the health information for forwarding based on the lack of the defined level of medical proficiency of the second contact identity;

receiving, by the system, second input information relating to a second portion of the health information for forwarding based on the defined level of medical proficiency of the third contact identity;

in response to receiving the health information, parsing, by the system, the health information to a parsed first portion according to the first input information;

in response to receiving the health information, parsing, by the system, the health information to a parsed second portion according to the second input information;

forwarding, by the system, the parsed first portion of the health information to the second mobile phone; and forwarding, by the system, the parsed second portion of the health information to the third mobile phone.

19. The method according to claim 18, further comprising:
determining, by the system, that the health associated with the subscriber identity is in an emergency condition based on processing the health data.

20. The method of claim 19, further comprising:
notifying, by the system, a device of a notification center of the emergency condition, wherein the emergency condition is determined based on analyzing health measurement data comprising identifying a pattern in a historical set of the health data.

21. The method of claim 1, further comprising:
pre-processing, by the mobile phone, prior to transmission by the mobile phone to the health data server, the health data as stored by the health data measuring device, wherein the pre-processing comprises compressing the health data.

22. The mobile phone according to claim 13, wherein the operations further comprise:
delivering a request to the health station server for a medical software update for the health measuring device; and
receiving the medical software update via the network device of the wireless wide area network from the health station server.

23. The method of claim 18, further comprising:
processing, by the system, the health data; and
detecting, by the system, a false positive indication of a specified activity of the subscriber identity based on comparing a portion of the health data received by the system with a defined aberration associated with the health data, the defined aberration indicating the portion of the health data is determined to be a false alarm.

24. The method of claim 21, wherein the pre-processing further comprises encrypting the health data.

25. The mobile phone of claim 13, wherein the operations further comprise enabling access by the mobile phone to the health data service associated with the health station server based on collection of the health data.

26. The method of claim 1, further comprising:
transmitting, by the mobile phone, to the health data server, a request to present a second subset of the health data on a third mobile phone associated with a medical-professional identity, wherein, in response to the request to present the second subset of the health data, the health data server filters the health data to generate the second subset of health data, based on a filter in connection with the request to present the second subset of the health data being associated with the medical-professional identity, and forwards the second subset of the health data to the third mobile phone.

* * * * *